US012693174B2

(12) United States Patent
Lee et al.

(10) Patent No.: US 12,693,174 B2
(45) Date of Patent: Jul. 28, 2026

(54) ELECTRONIC DEVICE AND METHOD OF MEASURING BODY TEMPERATURE USING THE SAME

(71) Applicant: SAMSUNG ELECTRONICS CO., LTD., Suwon-si (KR)

(72) Inventors: So Young Lee, Suwon-si (KR); Bok Soon Kwon, Suwon-si (KR); Sang Kyu Kim, Suwon-si (KR); Sung Ho Kim, Suwon-si (KR); Ho Taik Lee, Suwon-si (KR); Hong Soon Rhee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 488 days.

(21) Appl. No.: 17/979,372

(22) Filed: Nov. 2, 2022

(65) Prior Publication Data

US 2023/0400363 A1     Dec. 14, 2023

(30) Foreign Application Priority Data

Jun. 13, 2022     (KR) ......................... 10-2022-0071715

(51) Int. Cl.
*G01K 13/20*     (2021.01)
*A61B 5/00*     (2006.01)
          (Continued)

(52) U.S. Cl.
CPC ............... *G01K 13/20* (2021.01); *A61B 5/01* (2013.01); *A61B 5/681* (2013.01); *A61B 5/742* (2013.01);
          (Continued)

(58) Field of Classification Search
CPC .......... G01K 13/20; G01K 7/427; A61B 5/01; A61B 5/681; A61B 5/742;
          (Continued)

(56) References Cited

U.S. PATENT DOCUMENTS 6,846,106 B1 *     1/2005   Chen ....................... A61B 5/01
                                                    340/407.1
7,249,883 B2     7/2007   Kuroda et al.
                  (Continued)

FOREIGN PATENT DOCUMENTS

EP          4 027 124 A1     7/2022
JP       2012237670 A   * 12/2012   ............... A61B 5/01
                  (Continued)

OTHER PUBLICATIONS

Communication dated Jun. 23, 2023 by the European Patent Office in counterpart EP Patent Application No. 22211171.8.

*Primary Examiner* — Kristina M Deherrera
*Assistant Examiner* — Evan Mancini
(74) *Attorney, Agent, or Firm* — Sughrue Mion, PLLC

(57)          ABSTRACT

An electronic device for estimating body temperature is provided. The electronic device according to an embodiment of the present disclosure includes: a first temperature sensor configured to measure a first temperature of body skin; a second temperature sensor configured to measure a second temperature at a position spaced apart from the body skin; and a processor configured to estimate a body temperature based on the first temperature, to estimate an ambient temperature of a main body based on the second temperature, to calculate a heat loss, which occurs from a reference body location to the body skin due to the ambient temperature of the main body, based on the estimated ambient temperature of the main body, and to obtain a final body temperature by correcting the body temperature based on the heat loss due to the ambient temperature of the main body.

14 Claims, 21 Drawing Sheets

(51) Int. Cl.
    *A61B 5/01*        (2006.01)
    *G01K 7/42*       (2006.01)

(52) U.S. Cl.
    CPC ...... *G01K 7/427* (2013.01); *A61B 2560/0252*
        (2013.01); *A61B 2562/0271* (2013.01); *A61B*
        *2562/04* (2013.01)

(58) Field of Classification Search
    CPC .... A61B 2560/0252; A61B 2562/0271; A61B
        2562/04; A61B 5/0008; A61B 5/6824;
        A61B 5/6831
    USPC .......................................... 374/120; 600/549
    See application file for complete search history.

(56)          References Cited

U.S. PATENT DOCUMENTS

| | | | |
|---|---|---|---|
| 7,299,090 | B2 | 11/2007 | Koch |
| 9,357,929 | B2 | 6/2016 | Paquet |
| 10,368,811 | B1 | 8/2019 | Bajaj et al. |
| 10,765,409 | B2 | 9/2020 | Lafon et al. |
| 11,109,764 | B2 | 9/2021 | Bongers et al. |
| 11,224,344 | B2 * | 1/2022 | Ellis .................. A61B 5/02055 |
| 2011/0133939 | A1 * | 6/2011 | Ranganathan ....... A61B 5/6814 |
| | | | 340/584 |

| | | | | |
|---|---|---|---|---|
| 2012/0109571 | A1 * | 5/2012 | Shimizu ................. | G01K 13/20 |
| | | | | 702/130 |
| 2012/0109572 | A1 * | 5/2012 | Shimizu ................. | G01K 13/20 |
| | | | | 702/131 |
| 2016/0245706 | A1 * | 8/2016 | Zivkovic ............. | H04M 17/026 |
| 2019/0142280 | A1 | 5/2019 | Bongers et al. | |
| 2019/0350462 | A1 | 11/2019 | Biederman et al. | |
| 2019/0388031 | A1 * | 12/2019 | Haber ................... | G01K 1/165 |
| 2020/0323435 | A1 | 10/2020 | Selvaraj et al. | |
| 2021/0123819 | A1 | 4/2021 | Seyama et al. | |
| 2021/0204819 | A1 | 7/2021 | Kim et al. | |

FOREIGN PATENT DOCUMENTS

| | | | | |
|---|---|---|---|---|
| JP | 5898204 | B2 | 4/2016 | |
| JP | 2017-55968 | A | 3/2017 | |
| JP | 6957402 | B2 | 11/2021 | |
| KR | 10-2020-0021711 | A | 3/2020 | |
| KR | 10-2209494 | B1 | 1/2021 | |
| KR | 10-2021-0121356 | A | 10/2021 | |
| KR | 10-2021-0121359 | A | 10/2021 | |
| KR | 10-2021-0121360 | A | 10/2021 | |
| KR | 10-2021-0121361 | A | 10/2021 | |
| WO | WO-2010103436 | A1 * | 9/2010 | ............. G01K 13/20 |
| WO | 2021/057873 | A1 | 4/2021 | |

* cited by examiner

ELECTRONIC DEVICE AND METHOD OF MEASURING BODY TEMPERATURE USING THE SAME

CROSS-REFERENCE TO RELATED APPLICATION(S)

This application claims priority from Korean Patent Application No. 10-2022-0071715, filed on Jun. 13, 2022, in the Korean Intellectual Property Office, the disclosure of which is incorporated herein by reference in its entirety.

BACKGROUND

1. Field

Apparatuses and methods consistent with example embodiments relate to measuring body temperature using an electronic device.

2. Description of the Related Art

Generally, body temperature is one of four vital signs and has very important clinical significance. A body temperature sensor may be applied to various applications, such as checking infections in patients, thermal side effects of medications, or time of ovulation in women, and the like. However, there is a difference between skin temperature and core body temperature, such that it is difficult to measure the core body temperature by using a portable device such as a wearable device. A general body temperature sensor may be classified into a contact type sensor and a non-contact type sensor. Examples of the contact type sensor may include a sensor for detecting a change in electrical resistance, such as a Resistance Temperature Detector (RTD), a thermistor, etc., a thermocouple for detecting electromotive force, and the like. Further, examples of the non-contact type sensor may include a thermopile, a micro-bolometer, etc., which measure body temperature by detecting infrared rays radiating from a body surface. A general body temperature measurement technology is significantly affected by a change in environment factors affecting heat transfer, such as a change in external ambient temperature, humidity, air flow, and the like.

SUMMARY

Example embodiments address at least the above problems and/or disadvantages and other disadvantages not described above. Also, the example embodiments are not required to overcome the disadvantages described above, and may not overcome any of the problems described above.

According to an aspect of the present disclosure, there is provided an electronic device including: a first temperature sensor configured to measure a first temperature of body skin; a second temperature sensor configured to measure a second temperature at a position spaced apart from the body skin; and a processor configured to estimate a body temperature based on the first temperature, to estimate an ambient temperature of a main body based on the second temperature, to calculate a heat loss, which occurs from a reference body location to the body skin due to the ambient temperature of the main body, based on the estimated ambient temperature of the main body, and to obtain a final body temperature by correcting the body temperature based on the heat loss due to the ambient temperature of the main body.

The processor may estimate the body temperature by inputting the measured first temperature to a body temperature estimation model.

The processor may estimate the ambient temperature of the main body based on a difference between the first temperature and the second temperature.

The electronic device may further include a third temperature sensor disposed further away from the first temperature sensor than the second temperature sensor and configured to measure a third temperature, wherein the processor may estimate the ambient temperature of the main body based on at least one of a difference between the first temperature and the third temperature and a difference between the second temperature and the third temperature.

The first temperature sensor may be a non-contact temperature sensor including an infrared temperature sensor, and the second and third temperature sensors may be contact-type temperature sensors including a thermistor.

The processor may calculate the heat loss due to the ambient temperature of the main body based on a difference between a reference temperature, corresponding to the reference body location, and the ambient temperature of the main body.

The processor may calculate a heat loss by radiation based on the first temperature and the ambient temperature of the main body, and may obtain the final body temperature by correcting the estimated body temperature based on the heat loss due to the ambient temperature of the main body and the heat loss by radiation.

The processor may control continuous measurement by the first temperature sensor and the second temperature sensor, and may automatically obtain the final body temperature continuously based on the first temperature and the second temperature which are continuously measured.

The processor may control continuous measurement by the first temperature sensor and the second temperature sensor, may determine whether to update body temperature based on the continuously measured first and second temperatures, and may obtain the final body temperature again when update is required.

In addition, the electronic device may further include an output interface configured to output at least one of the first temperature, the second temperature, the ambient temperature of the main body, the final body temperature, a temperature measurement state, and guidance information related to body temperature.

According to another aspect of the present disclosure, there is provided a method of estimating body temperature, the method including: obtaining a first temperature of body skin; obtaining a second temperature that is measured at a position spaced apart from the body skin; estimating a body temperature based on the first temperature; estimating an ambient temperature of a main body based on the second temperature; calculating a heat loss, which occurs from a reference body location to the body skin due to the ambient temperature of the main body, based on the estimated ambient temperature of the main body; and obtaining a final body temperature by correcting the body temperature based on the heat loss due to the estimated ambient temperature of the main body.

The estimating of the body temperature may include estimating the body temperature by inputting the measured first temperature to a body temperature estimation model.

The estimating of the ambient temperature of the main body may include estimating the ambient temperature of the main body based on a difference between the first temperature and the second temperature.

The first temperature and the second temperature may be measured by a first temperature sensor and a second temperature sensor, respectively, and the method may further include obtaining a third temperature that is measured by a third temperature sensor disposed further away from the first temperature sensor than the second temperature sensor. The estimating of the ambient temperature of the main body may include estimating the ambient temperature of the main body based on at least one of a difference between the first temperature and the third temperature and a difference between the second temperature and the third temperature.

The calculating of the heat loss due to the ambient temperature of the main body may include calculating the heat loss due to the ambient temperature of the main body based on a difference between a reference temperature, corresponding to the reference body location, and the ambient temperature of the main body.

In addition, the method of estimating body temperature may further include calculating a heat loss by radiation based on the first temperature and the ambient temperature of the main body, wherein the obtaining of the final body temperature may include obtaining the final body temperature by correcting the estimated body temperature based on the heat loss due to the ambient temperature of the main body and the heat loss by radiation.

The estimating of the body temperature may include automatically and continuously repeating the measuring of the first temperature and following operations.

The first temperature and the second temperature may be received from an external device, and the external device may include a first temperature sensor and a second temperature sensor that measure the first temperature and the second temperature, respectively.

According to another aspect of the present disclosure, there is provided a wearable device including: a main body; a strap connected to the main body; a first temperature sensor configured to measure a skin temperature at a wrist when the main body is worn on the wrist; a second temperature sensor configured to measure an ambient temperature of the main body; and at least one processor configured to calculate a heat loss based on a difference between the skin temperature and the ambient temperature, and estimate a body temperature based on the skin temperature, the ambient temperature, and the heat loss.

While a wrist contact surface of the main body is in contact with the wrist, the processor may continuously repeat a process of obtaining the final body temperature.

In still another general aspect, there is provided an electronic device including: a memory for storing one or more instructions; a communication interface configured to receive a first temperature of body skin and a second temperature at a position spaced apart from the body skin, the first and second temperatures being measured by a temperature sensor; and a processor configured to estimate a body temperature of a user by executing the one or more instructions, wherein the processor is configured to estimate a body temperature based on the first temperature, to estimate an ambient temperature of a main body based on the second temperature, to calculate a heat loss, which occurs from a reference body location to the body skin due to the ambient temperature of the main body, based on the estimated ambient temperature of the main body, and to obtain a final body temperature by correcting the body temperature based on the heat loss due to the ambient temperature of the main body.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
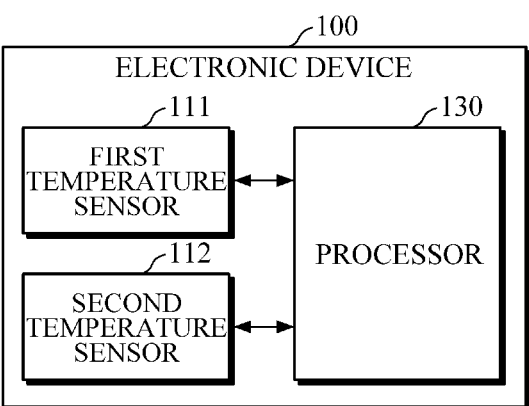
FIG. 1 is a block diagram illustrating an electronic device according to an embodiment of the present disclosure.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'unit' or 'module', etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

An electronic device according to various embodiments of the present disclosure which will be described below may include, for example, at least one of a wearable device, a smartphone, a tablet PC, a mobile phone, a video phone, an electronic book reader, a desktop computer, a laptop computer, a netbook computer, a workstation, a server, a PDA, a portable multimedia player (PMP), an MP3 player, a medical device, and a camera. The wearable device may include at least one of an accessory type wearable device (e.g., wristwatch, ring, bracelet, anklet, necklace, glasses, contact lens, or head mounted device (HMD)), a textile/clothing type wearable device (e.g., electronic clothing), a body-mounted type wearable device (e.g., skin pad or tattoo), and a body implantable type wearable device. However, the wearable device is not limited thereto and may include, for example, various portable medical measuring devices (antioxidant measuring device, blood glucose monitor, heart rate monitor, blood pressure measuring device, thermometer, etc.), magnetic resonance angiography (MRA), magnetic resonance imaging (MRI), computed tomography (CT), imaging system, ultrasonic system, etc.), and the like. However, the electronic device is not limited to the above devices.

Figure 2:
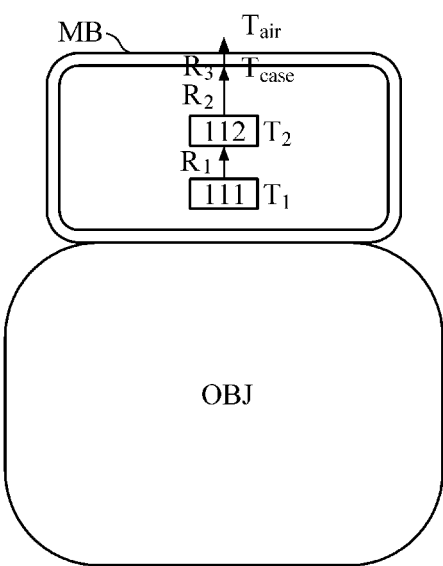
FIG. 2 is a diagram schematically illustrating the arrangement of temperature sensors in the electronic device according to the embodiment of FIG. 1.
Figure 3:
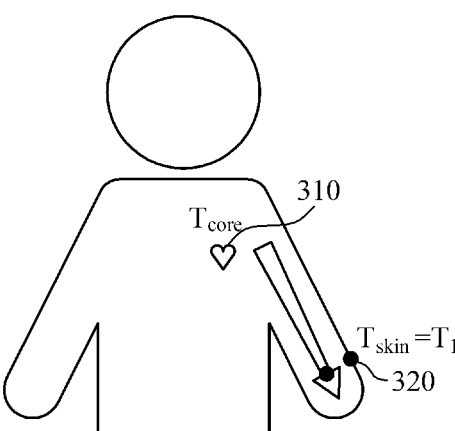
FIG. 3 is a diagram explaining an example of estimating body temperature and reflecting the effect of ambient temperature of a main body.

FIG. 1 is a block diagram illustrating an electronic device according to an embodiment of the present disclosure. FIG. 2 is a diagram schematically illustrating the arrangement of temperature sensors in the electronic device according to the embodiment of FIG. 1. FIG. 3 is a diagram explaining an example of estimating body temperature and reflecting the effect of ambient temperature of a main body. In the following description, the term "ambient temperature of the main body" may refer to an ambient air temperature outside of the main body, and may refer to an air temperature range that affects heat loss during estimation of body temperature.

Referring to FIG. 1, an electronic device 100 includes a first temperature sensor 111, a second temperature sensor 112, and a processor 130.

As illustrated in FIG. 2, the first temperature sensor 111 may be disposed on a surface of a main body case MB that comes into contact with a body OBJ (hereinafter referred to as a "first surface" or "skin surface") or may be disposed at a position adjacent to the first surface, and may measure a body skin temperature (hereinafter referred to as a "first temperature" or "skin temperature") during contact with the body OBJ. The surface of the main body case MB that comes into contact with the body OBJ may be referred to as a contact surface of the electronic device 100. In this case, a position of the object may be a surface of the wrist that is adjacent to the radial artery and an upper part of the wrist where venous blood or capillary blood passes, or a peripheral part of the body with high blood vessel density, such as fingers, toes, or ears. However, the position of the object is not limited thereto.

The second temperature sensor 112 may be disposed inside the main body case MB at a position spaced apart from the first temperature sensor 111. As illustrated in FIG. 2, the second temperature sensor 112 may be disposed relatively further away from the first surface of the main body case MB than the first temperature sensor 111, and may measure temperature inside the main body MB (hereinafter referred to as a "second temperature").

The first temperature sensor 111 and the second temperature sensor 112 may be attached to one or more structures (e.g., printed circuit board (PCB), battery, etc.) in the main body case MB. The first temperature sensor 111 and the second temperature sensor 112 may be disposed in a straight line, but the arrangement thereof is not limited thereto, and by changing the arrangement of structures, the first and second temperature sensors may be spaced apart at various positions. The first temperature sensor 111 may be disposed at a distance of mm or less from the first surface of the main body case MB, and the second temperature sensor 112 may be disposed at a distance of 10 mm or less from the first temperature sensor 111. However, distances and positions in the arrangement of the first and second temperature sensors 111 and 112 may be changed variously depending on the size and shape of a form factor and the like.

A thermally conductive material may be further disposed between the first temperature sensor 111 and the second temperature sensor 112, and/or on a surface that is opposite to the first surface (hereinafter referred to as a "second surface"). The first temperature sensor 111, the second temperature sensor 112, and the thermally conductive material may be formed in a stacked structure. The thermally conductive material may be, for example, a material (e.g., polyurethane foam) having a thermal conductivity of 0.1 W/mK or less. However, the size and thermal conductivity of the thermally conductive material are not limited thereto. Further, an air-filled structure may also be provided in which air having a low thermal conductivity is filled, without using a separate thermally conductive material.

The first temperature sensor 111 may be a non-contact temperature sensor (e.g., an infrared temperature sensor), and the second temperature sensor 112 may be a contact-type temperature sensor (e.g., a thermistor). Alternatively, both the first temperature sensor 111 and the second temperature sensor 112 may be the contact-type temperature sensors (e.g., a thermistor pair).

The processor 130 may be electrically connected to the first and second temperature sensors 111 and 112 to control the temperature sensors 111 and 112, and may estimate a user's body temperature by using temperature data received from the temperature sensors 111 and 112. Here, the body temperature may refer to a core temperature at a body reference location (e.g., heart), and may be defined as, for example, pulmonary arterial temperature while blood is pumped from the heart.

Referring to FIG. 3, the processor 130 may estimate body temperature based on a first temperature $T_1$ of body skin which is measured by the first temperature sensor 111 from a wrist 320 as a peripheral body part. The processor 130 may estimate the body temperature by inputting the first temperature $T_1$ to a pre-defined body temperature estimation model. The body temperature estimation model may be a model for converting the body skin temperature into a core temperature, and may be defined in the form of a linear/non-linear function by analyzing a correlation between the body skin temperature and the core temperature. In this case, if the first temperature sensor 111 is, for example, an infrared temperature sensor, the processor 130 may use an algorithm for converting skin temperature that is measured by the infrared temperature sensor, into body temperature.

Generally, while blood is pumped from the heart into the arteries, heat loss may occur through the skin due to the effect of ambient temperature of the main body. In this case, the heat loss may occur by radiation, convection, conduction, evaporation, and the like.

Accordingly, upon estimating the body temperature based on the first temperature $T_1$ measured at the skin of the peripheral body part 320, the processor 130 may correct the estimated body temperature based on the heat loss due to the effect of the ambient temperature of the main body, to obtain an accurate final body temperature value corresponding to the reference body location 310. The processor 130 may correct the estimated body temperature based on the heat loss, or may estimate the body temperature based on the heat loss as well as the skin temperature.

For example, the processor 130 may estimate the ambient temperature of the main body based on the second temperature measured by the second temperature sensor 112, and may obtain a heat loss due to the effect of the ambient temperature of the main body by using the estimated ambient temperature of the main body. Referring to FIG. 2, the processor 130 may estimate a heat flux based on the first temperature $T_1$ and the second temperature $T_2$, and may estimate the ambient temperature of the main body by using the estimated heat flux and the second temperature $T_2$.

Assuming that a flow of heat is a current, a heat transfer property of a material is resistance, and a heat flux is a voltage, the flow of heat may be expressed by an equation according to Bohr's law (V=IR). In this case, assuming heat transfer from the wrist to the second surface of the main body case in a series circuit, a heat flux may be estimated based on a difference $(T_1-T_2)$ between the first temperature $T_1$ and the second temperature $T_2$, and the following Equation 1 may be derived according to Ohm's law (V=IR). Equation 1 may be rewritten as the following Equation 2.

$$\frac{T_{case} - T_{air}}{R_3} = \frac{T_2 - T_{case}}{R_2} = \frac{T_1 - T_2}{R_1} \qquad \text{[Equation 1]}$$

$$T_{air} = T_2 - \frac{R_2 + R_3}{R_1}(T_1 - T_2) \qquad \text{[Equation 2]}$$

Herein, $T_{air}$ denotes the ambient temperature of the main body and air temperature outside the main body case; $T_{case}$ denotes the surface temperature of the thermally conductive material disposed between the second temperature sensor 112 and the second surface; $T_1$ and $T_2$ denote the first temperature and the second temperature, respectively; $R_1$ denotes a resistance of the thermally conductive material disposed between the first temperature sensor 111 and the second temperature sensor 112; $R_2$ denotes a resistance of the thermally conductive material disposed between the second temperature sensor 112 and the second surface; $R_3$ denotes a resistance of the main body case MB; and $$\frac{R_2 + R_3}{R_1}$$

denotes a heat transfer coefficient based on physical properties and is a value input in advance.

Upon estimating the ambient temperature of the main body, the processor 130 may calculate a heat loss from the reference body location 310 to the peripheral body part 320 due to the effect of the ambient temperature of the main body. For example, as illustrated in the following Equation 3, the processor 130 may calculate a difference between a reference body temperature at the reference body location and the estimated ambient temperature of the main body, and may obtain the heat loss due to the effect of the ambient temperature of the main body by applying a predefined coefficient to the calculated difference. In this case, the reference body temperature may be a fixed value, e.g., 36.5° C., which may be universally applied, and may be adjusted to values personalized for each user by considering the average body temperature of users, and the like.

$$T_{La} = \alpha(T_{cord} - T_{air}) \qquad \text{[Equation 3]}$$

Herein, $T_{La}$ denotes the heat loss due to the effect of the ambient temperature of the main body; $\alpha$ denotes a predefined coefficient; $T_{core}$ denotes a predefined reference body temperature; and $T_{air}$ denotes the ambient temperature of the main body.

Upon calculating the heat loss due to the effect of the ambient temperature of the main body, the processor 130 may obtain a final body temperature by correcting the body temperature, which is estimated based on the first temperature, for the heat loss due to the effect of the ambient temperature of the main body, as shown in the following Equation 4.

$$T_{b2} = T_{b1} + T_{La} \qquad \text{[Equation 4]}$$

Herein, $T_{b2}$ denotes the final body temperature corrected for the heat loss due to the ambient temperature of the main body; $T_{b1}$ denotes the body temperature estimated based on the first temperature; and $T_{La}$ denotes the heat loss due to the effect of the ambient temperature of the main body.

If the first temperature sensor 111 is an infrared temperature sensor, and the body temperature estimated based on the first temperature is estimated using a general infrared body temperature measurement technology, a heat loss by radiation may already be reflected in the estimated body temperature.

Accordingly, the processor 130 may calculate the heat loss by radiation based on the first temperature and the ambient temperature of the main body as shown in the following Equation 5, and may obtain the final body temperature by further subtracting the heat loss by radiation as shown in the following Equation 6.

$$T_{Lb} = \beta(T_1^4 - T_{air}^4) \qquad \text{[Equation 5]}$$

Herein, $T_{Lb}$ denotes the heat loss by radiation; $\beta$ denotes a predefined coefficient; and $$T_1^4 \text{ and } T_{air}^4$$

denote the fourth power of the first temperature and the ambient temperature of the main body, respectively.

$$T_{b2} = T_{b1} + T_{Lb} - T_{Lb} \qquad \text{[Equation 6]}$$

Herein, $T_{b2}$ denotes the final body temperature corrected for the heat loss due to the effect of the ambient temperature of the main body and the heat loss by radiation; $T_{b1}$ denotes the body temperature estimated based on the first temperature; $T_{La}$ denotes the heat loss due to the effect of the ambient temperature of the main body; and $T_{Lb}$ denotes the heat loss by radiation.

The aforementioned various embodiments of body temperature estimation may be performed continuously without a user's awareness. Here, the term "continuously" means that estimation not only continues at very short time intervals, but also is repeated at discrete time intervals (e.g., 1 min., 5 min., 1 h, etc.). In this case, there may be predetermined conditions for temperature measurement and/or body temperature estimation. The processor 130 may control the temperature sensors 111 and 112 according to the predetermined conditions, and may continuously estimate the body temperature by using temperature data measured by the temperature sensors 111 and 112.

For example, the temperature sensors 111 and 112 may continuously measure temperature while the electronic device 100 is turned on, and the processor 130 may estimate the body temperature in real time by receiving in real time the continuously measured temperature data from the temperature sensors 111 and 112.

In another example, the temperature sensors 111 and 112 and the processor 130 may continuously perform temperature measurement and body temperature estimation during a predetermined period of time (e.g., 30 min., 1 h, etc.) one or more times a day (e.g., 8 a.m., 2 p.m., 4 p.m., 10 p.m., every two hours, etc.).

In yet another example, the temperature sensors 111 and 112 may continuously measure temperature while the electronic device is turned on, and the processor 130 may estimate the body temperature at predetermined time intervals.

In yet another example, the temperature sensors 111 and 112 may continuously measure temperature while the electronic device is turned on, and the processor 130 may determine whether to update body temperature by analyzing the temperature data received in real time from the temperature sensors 111 and 112. That is, based on the analysis result, if the temperature data is normal, the processor 130 may determine that a body contact state is good and may continuously proceed with the body temperature estimation. For example, if predetermined conditions are satisfied, such as the case where a first temperature falls outside a first threshold range, the case where a second temperature falls outside a second threshold range, or the case where a difference between the first temperature and the second temperature falls outside a third threshold range, the processor 130 may determine that the temperature data is abnormal. Upon determining that the temperature data is abnormal, the processor 130 may provide guidance information so that the temperature measurement state may return to normal.

In yet another example, by analyzing sensor data collected from various sensors (e.g., camera, etc.) located inside the main body or at various positions of the main body case, the processor 130 may determine whether a body part is in contact with one surface of the main body, and may continuously measure temperature and/or estimate body temperature during the contact.

The above examples are provided merely for better understanding of continuous estimation, and the present disclosure is not limited thereto. In addition, various examples of body temperature estimation described in the present disclosure are not necessarily limited to continuous body temperature estimation without awareness, and an example of on-demand estimation of body temperature may also be possible in response to a user's request. Further, both the continuous estimation without awareness and the on-demand estimation may also be performed at the same time.

Figure 4:
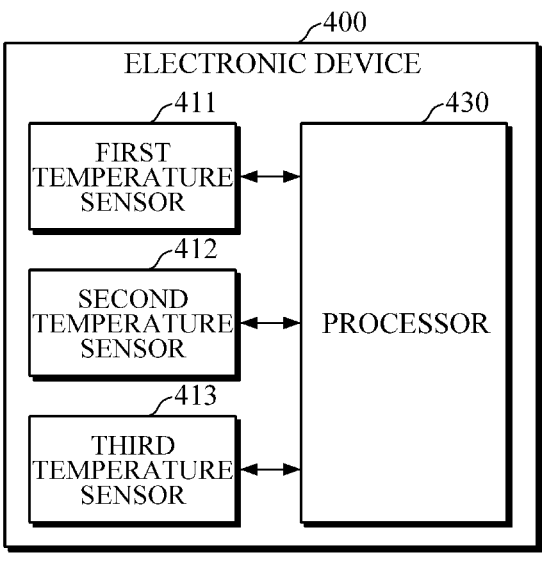
FIG. 4 is a block diagram illustrating an electronic device according to another embodiment of the present disclosure.
Figure 5:
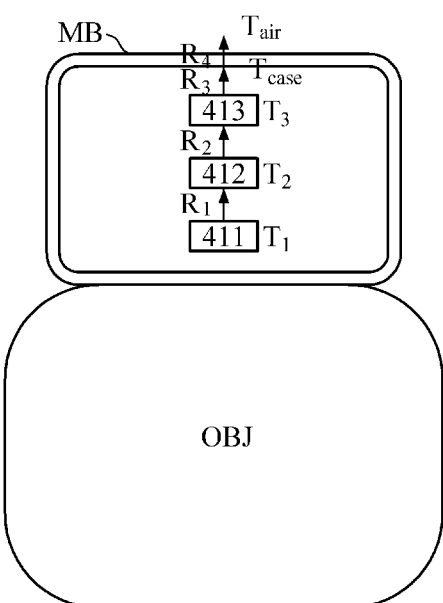
FIG. 5 is a diagram schematically illustrating the arrangement of temperature sensors in the electronic device according to the embodiment of FIG. 4.

FIG. 4 is a block diagram illustrating an electronic device according to another embodiment of the present disclosure. FIG. 5 is a diagram schematically illustrating the arrangement of temperature sensors in the electronic device according to the embodiment of FIG. 4.

Referring to FIG. 4, an electronic device 400 according to another embodiment includes a first temperature sensor 411, a second temperature sensor 412, a third temperature sensor 413, and a processor 430.

All of the first temperature sensor 411, the second temperature sensor 412, and the third temperature sensor 413 may be contact-type temperature sensors such as a thermistor. Alternatively, the first temperature sensor 411 may be a non-contact temperature sensor such as an infrared temperature sensor, and the second temperature sensor 412 and the third temperature sensor 413 may be a thermistor pair. In this case, the first temperature sensor 411, the second temperature sensor 412, and the third temperature sensor 413 may be separately formed. Alternatively, all the temperature sensors 411, 412, and 413 may be integrally formed as one module, or two temperature sensors 412 and 413 may integrally formed as one module.

Referring to FIG. 5, the first temperature sensor 411, the second temperature sensor 412, and the third temperature sensor 413 may be sequentially disposed at positions spaced apart from each other by a predetermined distance in a direction from a first surface, which is in contact with a body, toward a second surface, and may measure a first temperature, a second temperature, and a third temperature at the respective positions. In this case, at least two of the first temperature sensor 411, the second temperature sensor 412, and the third temperature sensor 413 may be disposed in a straight line, but the arrangement thereof is not limited thereto.

The temperature sensors 411, 412, and 413 may be attached to one or more structures (e.g., printed circuit board (PCB), battery, etc.) in the main body case MB.

A distance between the first temperature sensor 411 and the first surface of the main body case MB may be 0 mm to 10 mm, and a distance between the first temperature sensor 411 and the second temperature sensor 112 may be 0.5 mm to 10 mm. In addition, a distance between the second temperature sensor 412 and the third temperature sensor 413 may be 1 mm to 50 mm, and a distance between the third temperature sensor 413 and the second surface of the main body may be 10 mm or less. However, this is merely exemplary, and positions in the arrangement of the temperature sensors 411, 412, and 413 may be changed variously depending on the size of a form factor and the like by changing the arrangement of structures.

Thermally conductive materials may be further disposed between the respective temperature sensors 411, 412, and 413, and/or between the third temperature sensor 413 and the second surface. The thermally conductive materials may be, for example, insulators having a thickness of 0.1 mm to 50 mm, and may be materials (e.g., polyurethane foam) having a thermal conductivity of 0.1 W/mK or less. However, the size and thermal conductivity of insulators are not limited thereto. Further, an air-filled structure may also be provided without using a separate thermally conductive material.

Referring to FIG. 5, the first temperature sensor 411 may be disposed as close as possible to the contact surface, and the third temperature sensor 413 may be disposed as close as possible to the display panel to provide a relatively accurate temperature estimation.

The processor 430 may estimate body temperature by inputting the first temperature of the body skin, which is measured by the first temperature sensor 411, to a predefined body temperature estimation model. The body temperature estimation model for converting the body skin temperature into a core body temperature. If the first temperature sensor 411 is, for example, an infrared temperature sensor, a general technique for converting the skin temperature, measured by the infrared temperature sensor, into the body temperature may be used.

The processor 430 may estimate a heat flux based on a difference between the first temperature $T_1$, measured by the first temperature sensor 411, and the third temperature $T_3$ measured by the third temperature sensor 413, and/or a difference between the second temperature $T_2$, measured by the second temperature sensor 412, and the third temperature $T_3$ measured by the third temperature sensor 413, and may estimate the ambient temperature of the main body based on the relationship shown in the above Equation 1. The following Equation 7 shows an example of estimating the ambient temperature of the main body based on the difference between the second temperature and the third temperature.

$$T_{air} = T_3 - \frac{R_3 + R_4}{R_2}(T_2 - T_3) \qquad \text{[Equation 7]}$$

Herein, $T_{air}$ denotes the ambient temperature of the main body; $T_2$ and $T_3$ denote the second temperature and the third temperature, respectively; $R_2$ denotes a resistance of the thermally conductive material disposed between the second temperature sensor 412 and the third temperature sensor 413; $R_3$ denotes a resistance of the thermally conductive material disposed between the third temperature sensor 413 and the second surface; $R_4$ denotes a resistance of the main body case MB; and $$\frac{R_3 + R_4}{R_2}$$

denotes a heat transfer coefficient based on physical properties and is a value input in advance.

Upon estimating the ambient temperature of the main body, the processor 430 may calculate a heat loss from the reference body location to the peripheral body part due to the effect of the ambient temperature of the main body, based on the estimated ambient temperature of the main body as shown in the above Equations 3 and 4. The processor 430 may obtain a final body temperature by correcting the body temperature, which is estimated based on the first temperature, for the heat loss due to the effect of the ambient temperature of the main body. In this case, if the first temperature sensor 411 is an infrared temperature sensor and the body temperature is estimated based on the first temperature by using a general infrared body temperature estimation technology, the heat loss by radiation may be already reflected in the estimated body temperature, such that as shown in the above Equations 5 and 6, the processor 430 may obtain the heat loss by radiation, and may obtain the final body temperature by further subtracting the obtained heat loss by radiation.

Figure 6:
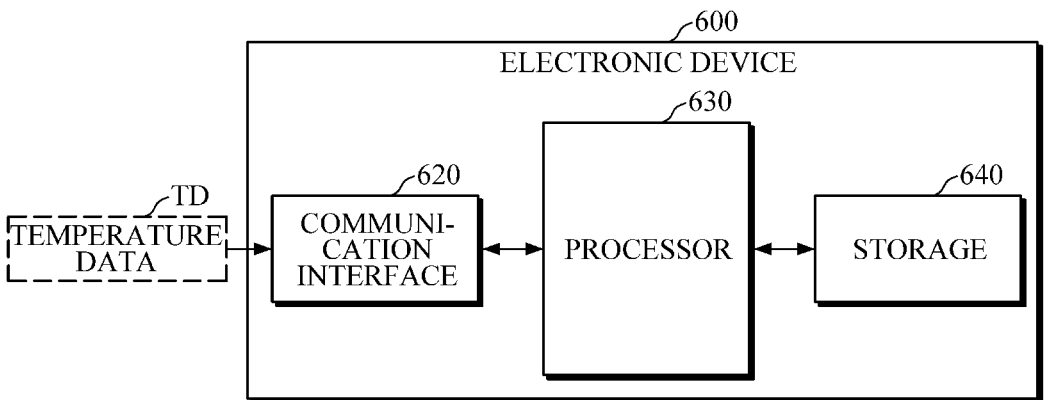
FIGS. 6 to 8 are block diagrams illustrating an electronic device according to other embodiments of the present disclosure.
Figure 7:
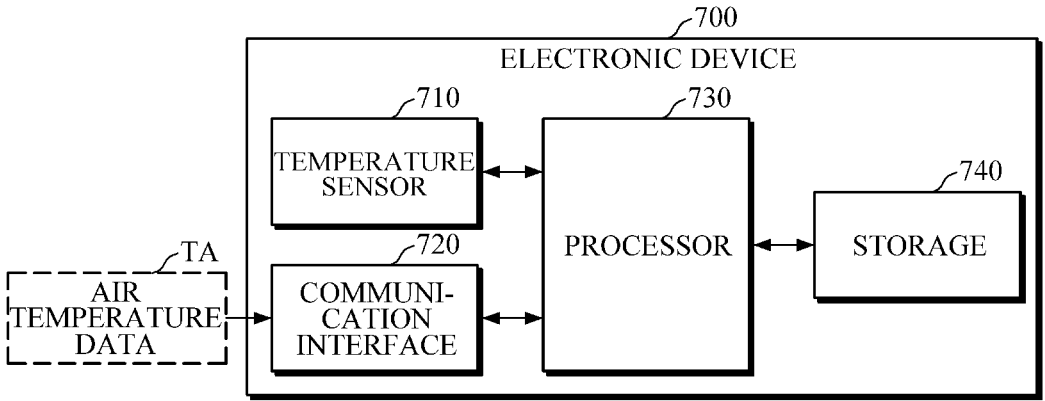
Figure 8:
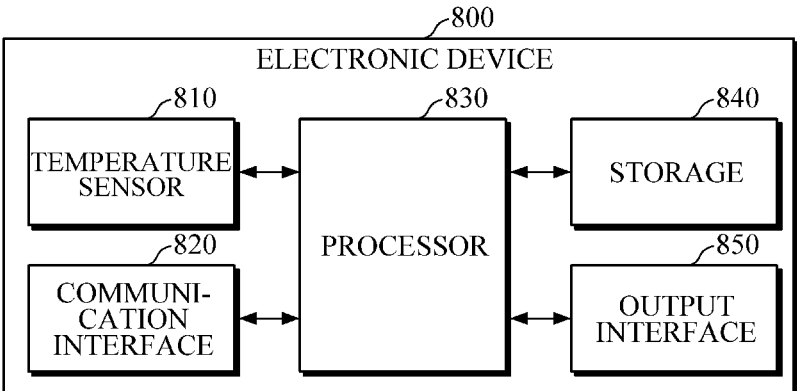

FIGS. 6 to 8 are block diagrams illustrating an electronic device according to other embodiments of the present disclosure.

Referring to FIG. 6, an electronic device 600 includes a communication interface 620, a processor 630, and a storage 640.

The communication interface 620 may receive temperature data TD, measured during contact with a user's body skin, from another electronic device including two or more temperature sensors. In addition, the communication interface 620 may transmit data, processed by the processor 630, to the electronic device.

The communication interface 620 may communication with the electronic device by using various wired and wireless communication techniques including Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G, 4G, and 5G communications, and the like. However, the communication techniques are not limited thereto.

The processor 630 may control the communication interface 620 and may estimate the body temperature by using the temperature data TD received through the communication interface 620, as described above. A detailed description thereof will be omitted. The processor 630 may execute instructions stored in the storage interface 640, and may estimate the body temperature by using reference data for body temperature estimation and/or user reference data.

The storage 640 may store various instructions. The storage 640 may store reference data for estimating body temperature, including a body temperature estimation model and a heat transfer coefficient, and/or user reference data including a user's age, stature, weight, exercise information, health information, and the like. Further, the storage 640 may store various data processed and generated by the electronic device 600.

The storage 640 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Referring to FIG. 7, an electronic device 700 includes a temperature sensor 710, a communication interface 720, a processor 730, and a storage 740.

The temperature sensor 710 may include a first temperature sensor disposed at a position adjacent to one surface of the main body which is in contact with the body, and configured to measure a body skin temperature during contact with the body. However, the temperature sensor 710 is not limited thereto and may further include a second temperature sensor and/or a third temperature sensor.

The communication interface 720 may receive air temperature data TA measured by an external temperature measuring device around the periphery of the main body. In addition, the communication interface 720 may transmit temperature data, measured by the temperature sensor 710 and/or data processed by the processor 730 to an external electronic device.

The processor 730 may estimate the body temperature based on the body skin temperature, measured by the temperature sensor 10, and the air temperature data TA outside the main body.

For example, as shown in the above Equations 3 to 6, the processor 730 may estimate the body temperature by using the body skin temperature and the data of ambient temperature of the main body. Alternatively, in the case where the temperature sensor 710 includes a plurality of temperature sensors, the processor 730 may estimate the ambient temperature of the main body by using the plurality of sensors as described above, and may correct (e.g., average, etc.) the estimated ambient temperature of the main body based on the data of air temperature outside the main body, which is received from the external temperature measuring device, thereby improving the accuracy of estimating body temperature.

The storage 740 may store various instructions. The storage 740 may store reference data for estimating body temperature, including a body temperature estimation model and a heat transfer coefficient, and/or user reference data including a user's age, stature, weight, exercise information, health information, and the like. Further, the storage 740 may store various data processed and generated by the electronic device 700.

Referring to FIG. 8, an electronic device 800 includes a temperature sensor 810, a communication interface 820, a processor 830, a storage 840, and an output interface 850.

The temperature sensor 810, the communication interface 820, the processor 830, and the storage 840 are described above, such that a detailed description thereof will be omitted, and the following description will be focused on non-redundant parts.

The processor 830 may determine a temperature measurement state based on temperature data, measured by the temperature sensor 810, and/or a final body temperature value. For example, if any one or two or more of first, second, and third temperatures fall outside each predetermined threshold range, the processor 830 may determine that the temperature measurement state is abnormal. Alternatively, if the final temperature value falls outside the threshold range, the processor 830 may determine that the temperature measurement state is abnormal.

In addition, if an estimated body temperature value falls outside a normal range, or by analyzing a body temperature estimation history during a predetermined period of time, the processor 830 may generate recommendation information, warning information, analysis information related to body temperature, and the like.

The output interface 850 may provide a user with information processed by the electronic device 800, such as the first temperature, second temperature, ambient temperature of the main body, final temperature, temperature measurement state, recommendation information, warning information, analysis information related to body temperature, etc., in a visual/non-visual manner by using a display, an audio output device, a haptic device, and the like.

FIGS. 9A to 9E are diagrams illustrating an example of providing information related to estimating body temperature in an electronic device.

Figure 9A:
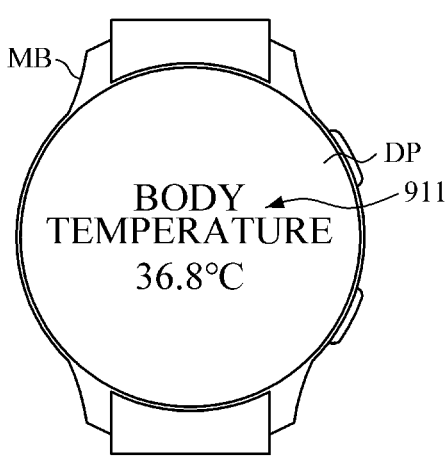
FIGS. 9A to 9E are diagrams illustrating an example of providing information related to estimating body temperature in an electronic device.
Figure 9B:
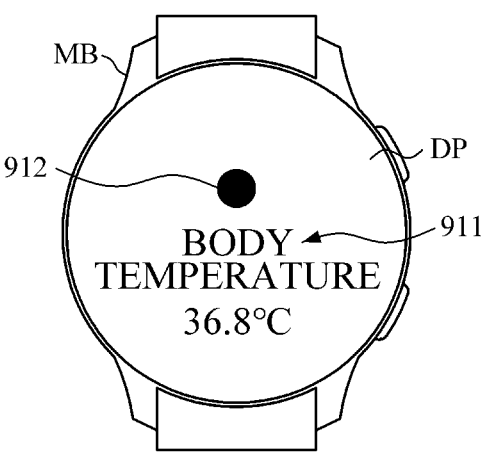
Figure 9C:
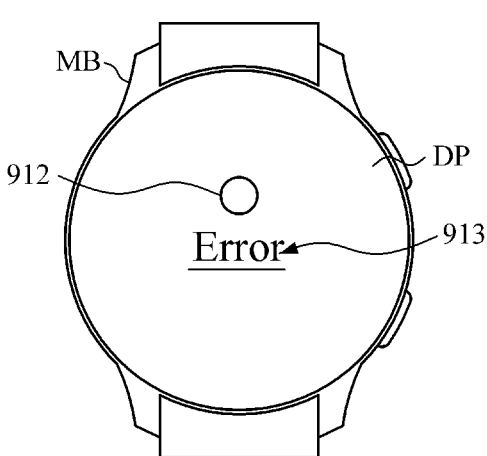

Referring to FIG. 9A, the output interface 850 may output body temperature information 911, estimated by the processor 830, to a display DP disposed on the main body MB. Referring to FIGS. 9B and 9C, a graphic object 912 indicating a temperature measurement state may be further displayed in addition to the body temperature information 911. FIG. 9B illustrates a case where the temperature measurement state is normal, and FIG. 9C illustrates a case where the temperature measurement state is abnormal, in which the temperature measurement states may be distinguished by displaying the graphic object 912 in different colors and the like, so that a user may easily recognize the temperature measurement states. In addition, if the temperature measurement state is abnormal, the output interface 850 may output an error message 113.

Figure 9D:
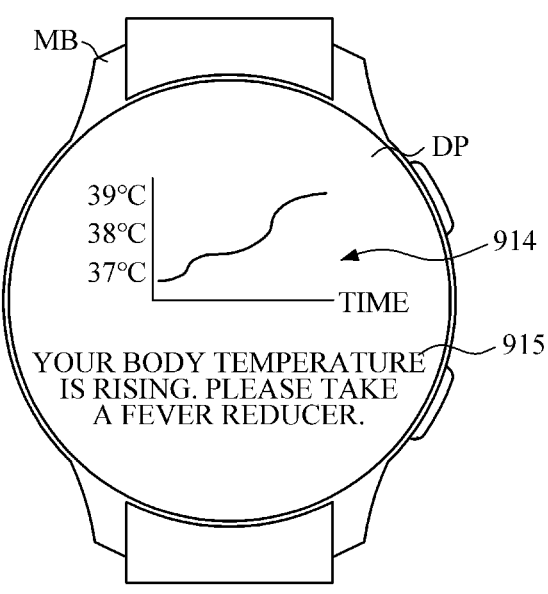
Figure 9E:
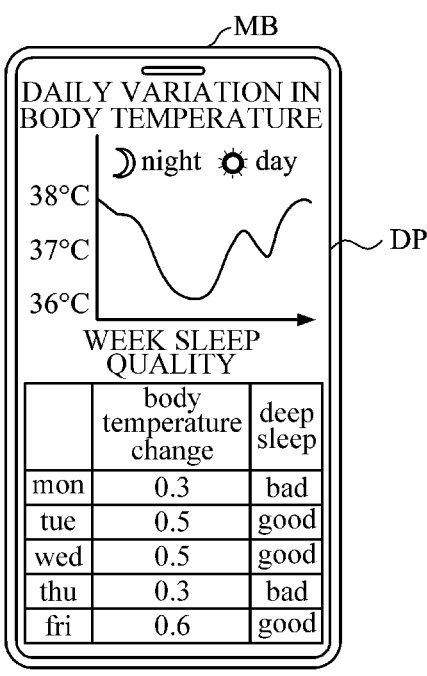

Referring to FIG. 9D, the output interface 850 may output a body temperature change graph 914 to the display DP, to allow a user to visually identify a change in continuous body temperature estimation during a predetermined period of time (one hour, a day, a week, etc.). In addition, as illustrated herein, if a body temperature change shows that the temperature rises above a threshold (e.g., 38° C.), the output interface 850 may output a recommended action 915 for the user to take. Referring to FIG. 9E, the output interface 850 may output a variety of analysis information, such as the estimated body temperature, a change of temperature during a day which is analyzed based on the body temperature estimation history during a predetermined period of time, a sleep quality related to the estimated body temperature, and the like.

Figure 10:
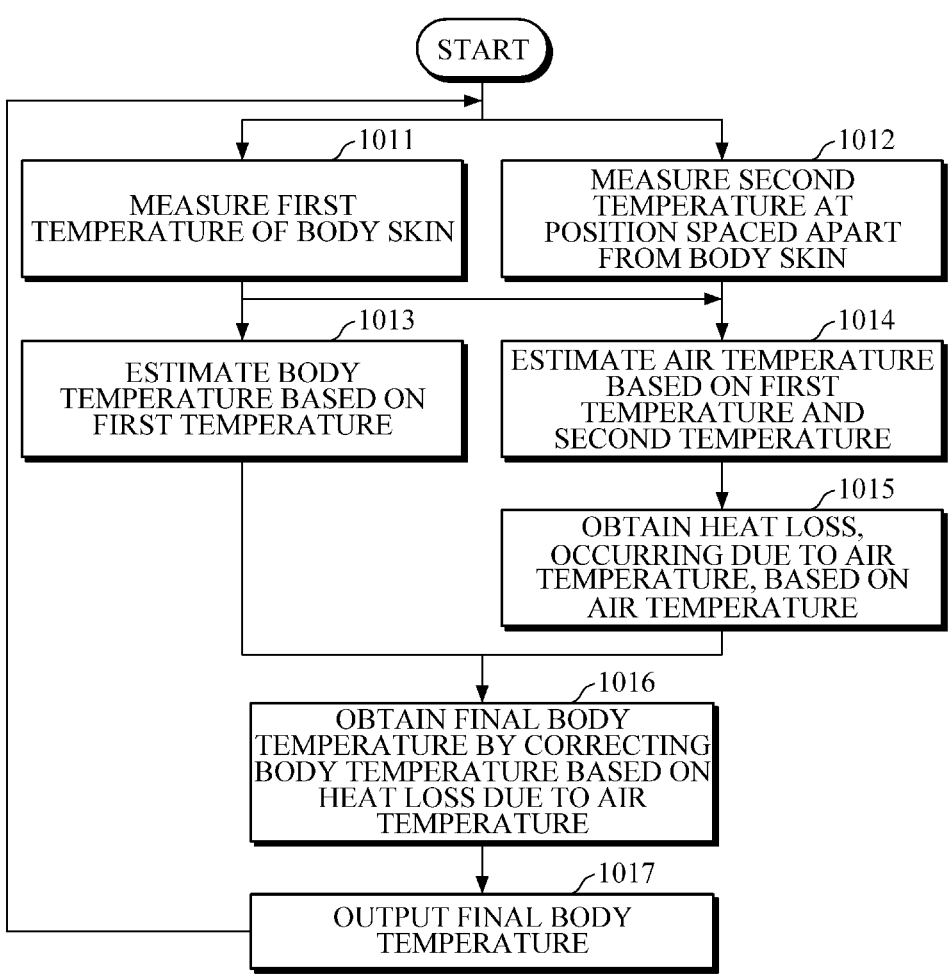
FIG. 10 is a flowchart illustrating a method of estimating body temperature according to an embodiment of the present disclosure.

FIG. 10 is a flowchart illustrating a method of estimating body temperature according to an embodiment of the present disclosure. The method of FIG. 10 is an example of a method of estimating body temperature performed by the electronic device 100 of FIG. 1, such that a detailed description thereof will be omitted.

The electronic device 100 may measure a first temperature of body skin during contact with the body by using the first temperature sensor disposed adjacent to the body contact surface of the main body case in 1011, and may measure a second temperature inside the main body in 1012 by using the second temperature sensor spaced apart from the first temperature sensor in the main body. In this case, both the first and second temperature sensors may be thermistor-based contact-type temperature sensors, or the first temperature may be an infrared-based non-contact temperature sensor.

Then, the electronic device 100 may estimate a body temperature based on the first temperature in 1013. The electronic device 100 may estimate the body temperature by inputting the first temperature to a body temperature estimation model. In this case, the body temperature estimation model may be pre-defined, and if the first temperature sensor is an infrared temperature sensor, the body temperature may be estimated using a general infrared body temperature estimation technology.

Subsequently, the electronic device 100 may estimate an ambient temperature of the main body based on the first temperature and the second temperature in 1014. As described above, the electronic device 100 may estimate a heat flux based on a difference between the first temperature and the second temperature, and may estimate the ambient temperature of the main body by using the estimated heat flux, a predefined heat transfer coefficient, and the second temperature.

Next, based on the ambient temperature of the main body which is estimated in 1014, the electronic device 100 may obtain a heat loss, occurring from a reference body location to a peripheral body part, at which the first temperature is measured, due to the effect of the ambient temperature of the main body in 1015. For example, the electronic device 100 may calculate a difference by subtracting the ambient temperature of the main body from a reference body temperature predetermined for the reference body location, and by applying a predefined coefficient to the calculated difference value, the electronic device 100 may obtain the heat loss due to the effect of the ambient temperature of the main body.

Then, the electronic device 100 may obtain a final body temperature in 1016 by correcting the body temperature, which is estimated in 1013, based on the heat loss obtained in 1015 due to the ambient temperature of the main body. In this case, if the body temperature estimated in 1013 is estimated using a general infrared temperature measurement technology, the electronic device 100 may further obtain a heat loss by radiation, and may further reflect the obtained heat loss by radiation.

Subsequently, the electronic device 100 may output information on the estimated body temperature in 1017, and may proceed to operations 1011 and 1012 again for measuring temperature.

Figure 11:
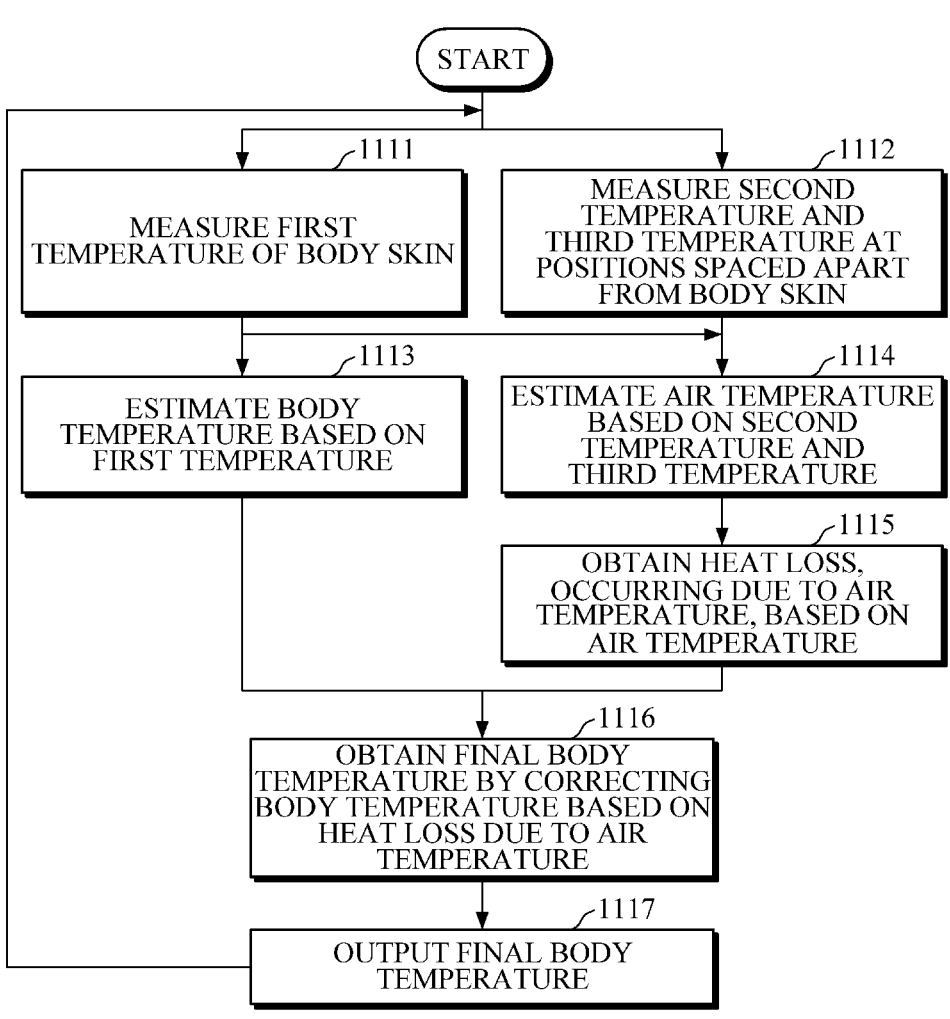
FIG. 11 is a flowchart illustrating a method of estimating body temperature according to another embodiment of the present disclosure.

FIG. 11 is a flowchart illustrating a method of estimating body temperature according to another embodiment of the present disclosure. The method of FIG. 11 is an example of a method of estimating body temperature performed by the electronic device 400 of FIG. 4, such that a detailed description thereof will be omitted.

The electronic device 400 may measure a first temperature of body skin during contact with the body by using the first temperature sensor disposed adjacent to the body contact surface of the main body case in 1111, and may measure second and third temperatures inside the main body in 1112 by using the second and third temperature sensors spaced apart at different distances from the first temperature sensor in the main body. In this case, all the temperature sensors may be thermistor-based contact-type temperature sensors, or the first temperature may be an infrared-based non-contact temperature sensor.

Then, the electronic device 400 may estimate a body temperature based on the first temperature in 1113.

Subsequently, the electronic device 400 may estimate the ambient temperature of the main body based on at least one of the first and second temperatures or the second and third temperatures in 1114. As described above, the electronic device 400 may estimate a heat flux based on a difference between the second temperature and the third temperature, and may estimate the ambient temperature of the main body by using the estimated heat flux, the predefined heat transfer coefficient, and the third temperature.

Next, the electronic device 400 may obtain a heat loss from a reference body location to a peripheral body part based on the estimated ambient temperature of the main body in 1115.

Then, the electronic device 400 may obtain a final body temperature in 1116 by correcting the body temperature, which is estimated in 1113, based on the heat loss obtained in 1115 due to the ambient temperature of the main body. In this case, the electronic device 400 may further reflect the heat loss by radiation as described above.

Subsequently, the electronic device 400 may output information on the estimated body temperature in 1117, and may proceed to operations 1111 and 1112 again for measuring temperature.

Figure 12:
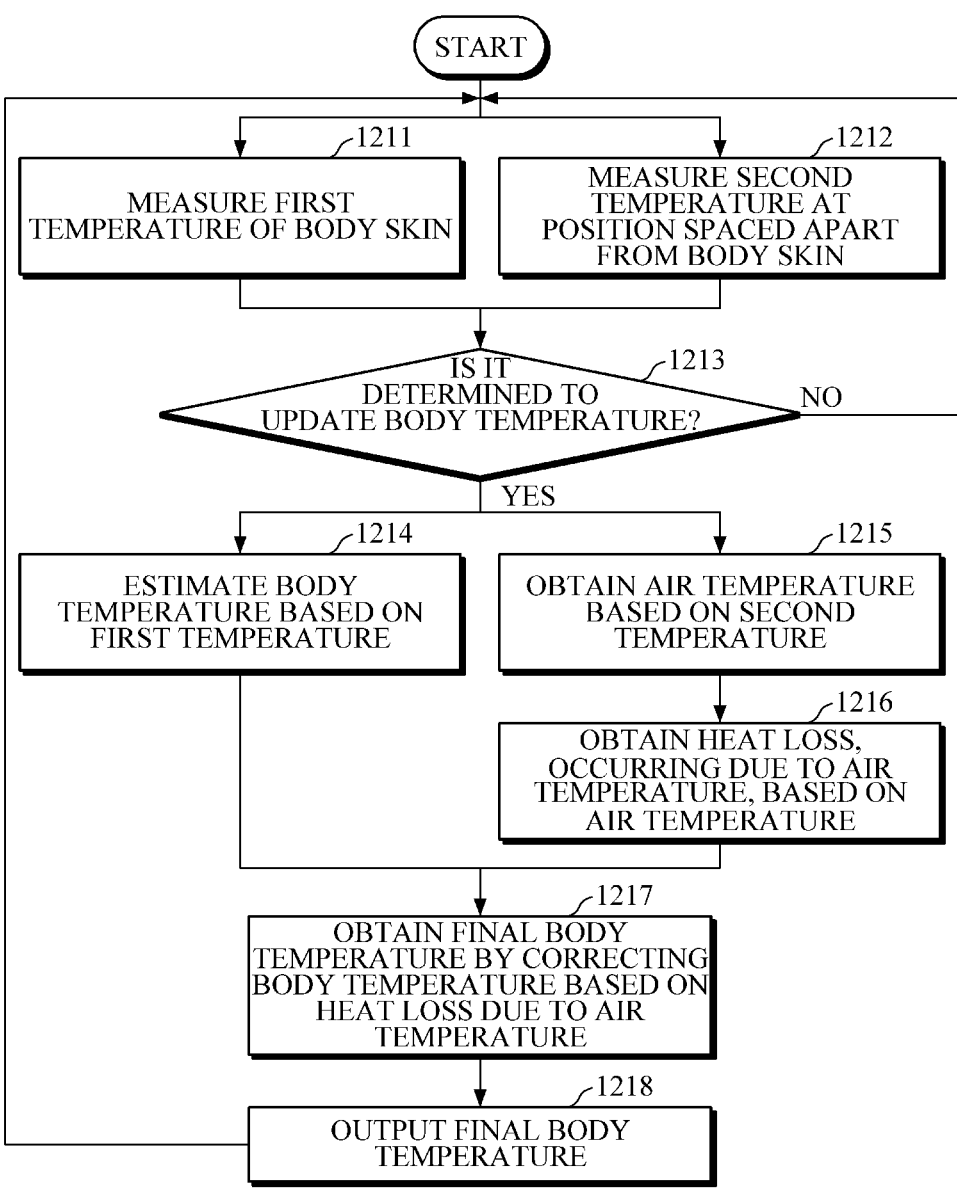
FIG. 12 is a flowchart illustrating a method of estimating body temperature according to yet another embodiment of the present disclosure.

FIG. 12 is a flowchart illustrating a method of estimating body temperature according to yet another embodiment of the present disclosure. The method of FIG. 12 is an example of a method of estimating body temperature performed by the electronic devices 100, 400, 600, 700, and 800 described above, and an example of continuous body temperature measurement.

The electronic device may measure a first temperature of body skin by using the first temperature sensor in 1211, and may measure a second temperature and/or a third temperature at one or more positions spaced apart from the body skin by using the second temperature sensor in 1212.

Then, the electronic device may determine whether to update body temperature based on the first temperature, second temperature. and/or third temperature in 1213. For example, if predetermined conditions are not satisfied, such as the case where a predetermined period of time does not elapse, the case where one or more of the first temperature, the second temperature, and/or the third temperature fall outside each predetermined threshold range, etc., the electronic device may determine that it is not required to update the body temperature, and may proceed to operations 1211 and 1212 for measuring temperature.

Upon determining in 1213 that it is required to update the body temperature, the electronic device may estimate the body temperature based on the first temperature in 1214, and may obtain the ambient temperature of the main body based on the first and second temperatures, the first and third temperatures, or the second and third temperatures in 1215.

Subsequently, the electronic device may obtain a heat loss due to air temperature in 1216 based on the ambient temperature of the main body which is obtained in 1215, and may obtain a final body temperature in 1217 by correcting the body temperature, which is estimated in 1213, based on the heat loss due to the ambient temperature of the main body.

Next, the electronic device may output, in 1218, the final body temperature obtained in 1217 and may proceed to operations 1211 and 1212 for measuring temperature.

FIGS. 13 to 16 are diagrams illustrating examples of structures of the above electronic devices 100, 400, 600, 700, and 800. However, the present disclosure is not limited to these illustrated examples.

Figure 13:
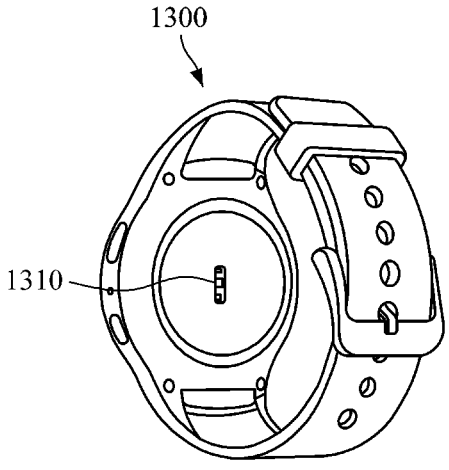
FIGS. 13 to 16 are diagrams illustrating examples of structures of an electronic device.

Referring to FIG. 13, the electronic device may be implemented as a watch-type wearable device which includes a main body and a wrist strap. A display may be provided on a front surface of the main body MB, and may display various application screens including time information, received message information, estimated body temperature information, and the like. A sensor device 1310 may be disposed on a rear surface of the main body. The sensor device 1310 may include a plurality of temperature sensors spaced apart at different distances from a wrist contact surface. In addition, the electronic device may include various other sensors, such as a PPG sensor and the like. A processor and various other components may be disposed in the main body case.

Figure 14:
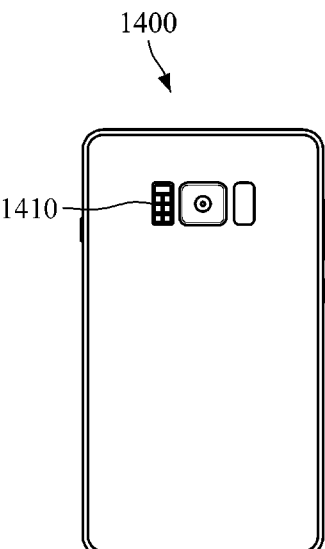

Referring to FIG. 14, the electronic device may be implemented as a mobile device 1400 such as a smartphone.

The mobile device 1400 may include a main body case and a display panel. The main body case may form an outer appearance of the mobile device 1400. The main body case has a front surface, on which the display panel and a cover glass may be disposed sequentially, and the display panel may be exposed to the outside through the cover glass. A sensor device 1410, a camera module and/or an infrared sensor, and the like may be disposed on a rear surface or a lateral surface of the main body. The sensor device 1410 may include a plurality of temperature sensors spaced apart at different distances from a contact surface with a body part (e.g., finger). A processor and various other components may be disposed in the main body case.

Figure 15:
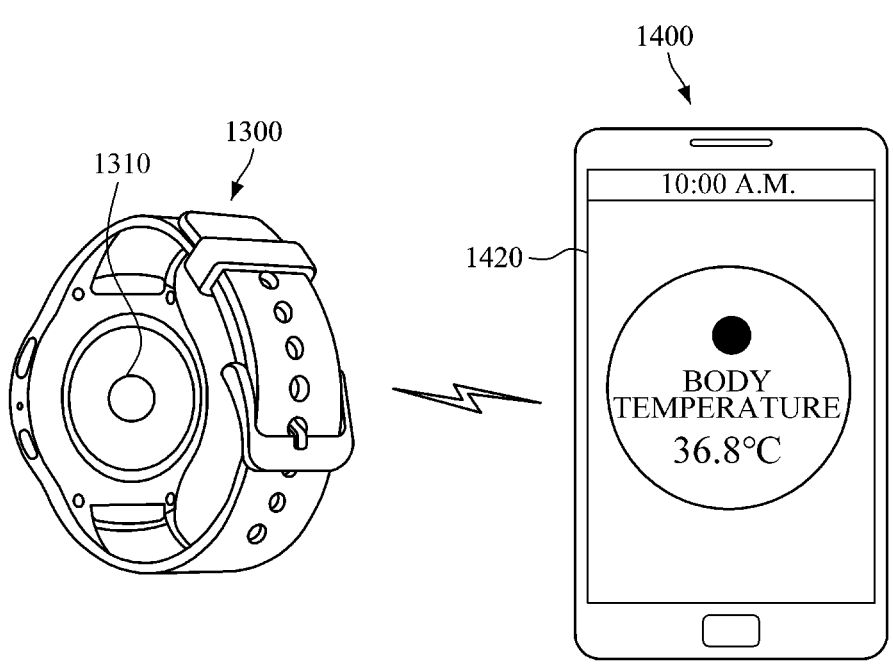

FIG. 15 is a diagram illustrating an example of estimating body temperature by connection between a smart watch 1300 and a smartphone 1400. For example, body temperature may be estimated by a processor and a temperature sensor 1310 of the smart watch 1300, and the smart phone 1400 may receive, through a communication interface, a body temperature estimation result and/or a temperature measurement state from the smart watch 1300 and may output the received data to a display 1420. In another example, temperature may be measured by the temperature sensor 1310 of the smart watch 1300, and the smartphone 1400 may receive temperature data from the smart watch 1300 to estimate body temperature and may output an estimation result. The opposite case is also possible.

Figure 16:
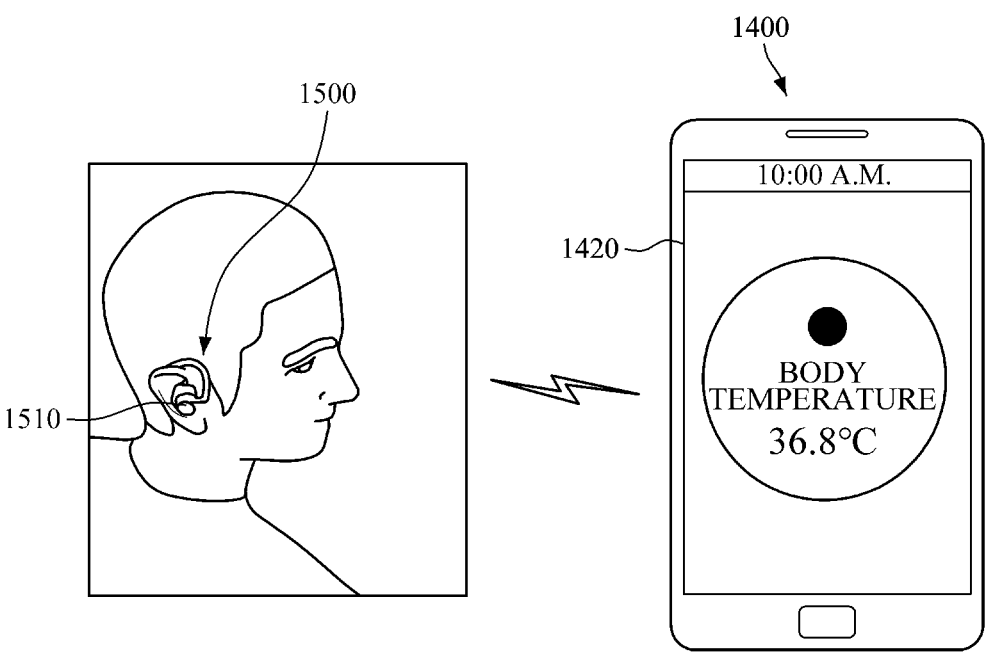

FIG. 16 is a diagram illustrating an example of estimating body temperature by connection between an ear-wearable deice 1500 and the smartphone 1400. For example, when a main body case of the ear-wearable device 1500 is worn on the ear, body temperature may be estimated by a processor and a temperature sensor 1510 of the ear-wearable device 1500, and the smartphone 1400 may receive a body temperature estimation result and/or a temperature measurement state and may output the received data to the display 1420. In another example, temperature may be measured by the temperature sensor 1510 of the ear-wearable device 1500, and the smartphone 1400 may receive temperature data from the ear-wearable deice 1500 to estimate body temperature and may output an estimation result.

Figure 17:
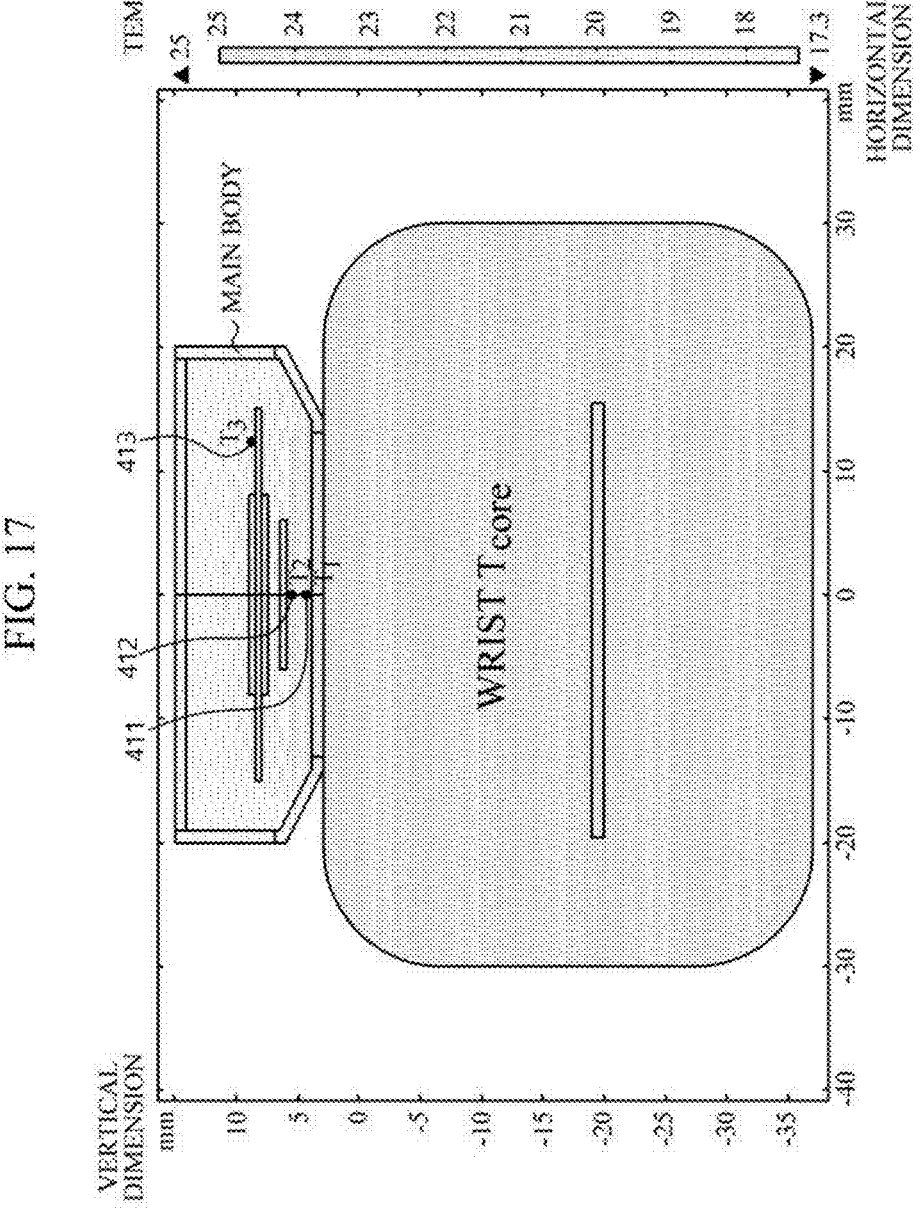
FIG. 17 illustrates a simulation result of estimating an air temperature according to an example embodiment of the present disclosure.

FIG. 17 illustrates a simulation result of estimating an air temperature according to an example embodiment of the present disclosure. Since a body temperature is estimated based on an estimated air temperature and an estimated core body temperature according to embodiments of the disclosure, the more accurate the estimated air temperature is, the more accurate the estimation of the body temperature is.

As shown in FIG. 17, a main body of an electronic device includes an upper surface and a lower surface. When the lower surface is in contact with a user's wrist, the body heat of the user may be conveyed to the lower surface of the main body, and then may transfer from the lower surface to the upper surface of the main body.

Referring to FIG. 17, the main body may include a first temperature sensor 411 and a second temperature sensor 412 that are arranged in a vertical direction (e.g., a thickness direction) of the main body. Also, the main body may include a third temperature sensor 413 which is located farther from the lower surface of the main body (e.g., a contact surface between the main body and the user's wrist) than the first temperature sensor 411 and the second temperature sensor 412. The first temperature sensor 411 may be disposed at a vertical distance (i.e., a thickness direction) of 5 mm or less from the contact surface, and the third temperature sensor 413 may be disposed at a vertical distance of 10 mm or less from the contact surface of the main body 110. In addition, a vertical distance between the first temperature sensor 411 and the second temperature sensor 412 may be 10 mm or less, and a vertical distance between the third temperature sensor 413 and the second temperature sensor 412 may be 10 mm to 50 mm. A first thermally conductive material may be provided between the first temperature sensor 411 and the second temperature sensor 412. A second thermally conductive material may be provided between the second temperature sensor 412 and the third temperature sensor 413. A third thermally conductive material may be provided between the third temperature sensor 413 and an upper surface 200 of the main body 110. Each or at least one of the first thermally conductive material, the second thermally conductive material, and the third thermally conductive material may be insulators having a minimum thickness of 0.4 mm or (i.e., 0.4 mm or greater, and preferably from 0.4 mm to 1.3 mm, and may be materials (e.g., polyurethane foam) having a thermal conductivity of 0.1 W/mK or low. Each of the first, second, and third temperatures sensors 411-413 may be set to have a minimum height of 0.3 mm (i.e., 0.3 mm or greater, and preferably from 0.3 mm to 0.5 mm).

When the first temperature sensor 411, the second temperature sensor 412, and the third temperature sensor 413 are arranged as described above, the electronic device may be capable of estimating an air temperature at a high accuracy as shown below:

| Temperature Sensor T3 | Temperature Sensor T2 | Actual Air Temperature | Estimated Air Temperature |
|---|---|---|---|
| 20.96° C. | 22.62° C. | 15° C. | 14.96° C. |
| 24.77° C. | 26.10° C. | 20° C. | 19.98° C. |
| 29.18° C. | 30.34° C. | 25° C. | 25.00° C. |
| 32.39° C. | 33.05° C. | 30° C. | 30.00° C. |

As shown above, the air temperatures that are estimated according to embodiments of the present disclosure are quite accurate since the differences between the estimated air temperatures and the actual air temperatures are 0.96° C., 0.02° C., 0.00° C., and 0.00° C.

According to embodiments of the present disclosure, the core body temperature of a user may be estimated continuously via an electronic device worn by the user, in real time while the electronic device measures the skin temperature of the user and the ambient temperature of the electronic device. Since the effect of the ambient temperature of a main body is reflected in estimating the core body temperature, the estimation accuracy of the core body temperature may be improved.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:
1. An electronic device comprising:
a first temperature sensor configured to measure a first temperature of body skin;

a second temperature sensor configured to measure a second temperature at a position spaced apart from the body skin;

a third temperature sensor disposed farther away from the first temperature sensor than the second temperature sensor and configured to measure a third temperature; and a processor configured to:

estimate a body temperature based on the first temperature;

estimate an ambient temperature of the electronic device based on a difference between the first temperature and the second temperature and based on at least one of a difference between the first temperature and the third temperature and a difference between the second temperature and the third temperature;

calculate a heat loss which occurs from a reference body location to the body skin due to the ambient temperature of the electronic device, based on the ambient temperature; and obtain a final body temperature by correcting the body temperature based on the heat loss, wherein the processor is further configured to calculate a heat loss by radiation based on the first temperature and the ambient temperature, and obtain the final body temperature by adding the estimated body temperature and the heat loss due to the ambient temperature and subtracting the heat loss by radiation, and wherein a vertical distance between the first temperature sensor and a surface of the body skin is less than or equal to 5 mm, a vertical distance between the first temperature sensor and the second temperature sensor is less than or equal to 10 mm, and a vertical distance between the second temperature sensor and the third temperature sensor is in a range of 10 mm to 50 mm.

2. The electronic device of claim 1, wherein the processor is further configured to estimate the body temperature by inputting the measured first temperature to a body temperature estimation model.

3. The electronic device of claim 1, wherein the first temperature sensor is a non-contact temperature sensor including an infrared temperature sensor, and the second temperature sensor and the third temperature sensor are contact-type temperature sensors including a thermistor.

4. The electronic device of claim 1, wherein the processor is further configured to calculate the heat loss due to the ambient temperature based on a difference between a reference temperature, corresponding to the reference body location, and the ambient temperature.

5. The electronic device of claim 1, wherein the processor controls a continuous measurement by the first temperature sensor and the second temperature sensor, and automatically obtains the final body temperature continuously based on the first temperature and the second temperature which are continuously measured.

6. The electronic device of claim 1, wherein the processor controls a continuous measurement by the first temperature sensor and the second temperature sensor, determines whether to update the body temperature based on the continuously measured first and second temperatures, and obtains the final body temperature again when update is required.

7. The electronic device of claim 1, further comprising an output interface configured to output at least one of the first temperature, the second temperature, the ambient temperature, the final body temperature, a temperature measurement state, and guidance information related to the body temperature.

8. A method of estimating body temperature, the method comprising:

obtaining, by a first temperature sensor, a first temperature of body skin;

obtaining, by a second temperature sensor, a second temperature that is measured at a position spaced apart from the body skin;

obtaining, by a third temperature sensor, a third temperature that is measured at a position farther away from the body skin than the position at which the second temperature is measured;

estimating a body temperature based on the first temperature;

estimating an ambient temperature based on a difference between the first temperature and the second temperature and based on at least one of a difference between the first temperature and the third temperature and a difference between the second temperature and the third temperature;

calculating a heat loss, which occurs from a reference body location to the body skin due to the ambient temperature, based on the estimated ambient temperature; and obtaining a final body temperature by correcting the body temperature based on the heat loss due to the estimated ambient temperature, wherein the method further comprises calculating a heat loss by radiation based on the first temperature and the ambient temperature, and obtaining the final body temperature by adding the estimated body temperature and the heat loss due to the ambient temperature and subtracting the heat loss by radiation, and wherein a vertical distance between the first temperature sensor and a surface of the body skin is less than or equal to 5 mm, a vertical distance between the first temperature sensor and the second temperature sensor is less than or equal to 10 mm, and a vertical distance between the second temperature sensor and the third temperature sensor is in a range of 10 mm to 50 mm.

9. The method of claim 8, wherein the estimating of the body temperature comprises estimating the body temperature by inputting the measured first temperature to a body temperature estimation model.

10. The method of claim 8, wherein the calculating of the heat loss due to the ambient temperature comprises calculating the heat loss due to the ambient temperature based on a difference between a reference temperature, corresponding to the reference body location, and the ambient temperature.

11. The method of claim 8, wherein the estimating of the body temperature comprises automatically and continuously repeating the measuring of the first temperature and following operations.

12. A wearable device comprising:

a main body;

a strap connected to the main body;

a first temperature sensor configured to measure a first temperature at a wrist when the main body is worn on the wrist;

a second temperature sensor configured to measure a second temperature of the main body;

a third temperature sensor disposed farther away from the
   first temperature sensor than the second temperature
   sensor and configured to measure a third temperature;
   and
at least one processor configured to:
   estimate an ambient temperature of the wearable device
      based on a difference between the first temperature
      and the second temperature and based on at least one
      of a difference between the first temperature and the
      third temperature and a difference between the sec-
      ond temperature and the third temperature;
   calculate a heat loss based on a difference between a
      skin temperature and the ambient temperature; and
   estimate a body temperature based on the skin tem-
      perature, the ambient temperature, and the heat loss,
wherein the processor is further configured to calculate a
   heat loss by radiation based on the first temperature and
   the ambient temperature, and obtain the body tempera-
   ture by adding the estimated body temperature and the
   heat loss due to the ambient temperature and subtract-
   ing the heat loss by radiation, and
wherein a vertical distance between the first temperature
   sensor and a surface of the body skin is less than or
   equal to 5 mm, a vertical distance between the first
   temperature sensor and the second temperature sensor
   is less than or equal to 10 mm, and a vertical distance
   between the second temperature sensor and the third
   temperature sensor is in a range of 10 mm to 50 mm.
   13. The wearable device of claim 12, wherein while a
wrist contact surface of the main body is in contact with the
wrist, the at least one processor is configured to automati-
cally repeat a process of obtaining the body temperature.
   14. An electronic device comprising:
   a memory for storing one or more instructions;
   a communication interface configured to receive a first
      temperature of body skin measured by a first tempera-
      ture sensor, a second temperature at a position spaced apart from the body skin measured by a second tem-
   perature sensor, and a third temperature that is mea-
   sured at a position farther away from the body skin than
   the position at which the second temperature is mea-
   sured by a third temperature sensor; and
a processor configured to estimate a body temperature of
   a user by executing the one or more instructions,
wherein the processor is configured to:
   estimate the body temperature based on the first tem-
      perature;
   estimate an ambient temperature of a main body based
      on a difference between the first temperature and the
      second temperature and based on at least one of a
      difference between the first temperature and the third
      temperature and a difference between the second
      temperature and the third temperature;
   calculate a heat loss, which occurs from a reference
      body location to the body skin due to the ambient
      temperature of the main body, based on the estimated
      ambient temperature of the main body; and
   obtain a final body temperature by correcting the body
      temperature based on the heat loss due to the ambient
      temperature of the main body, and
wherein the processor is further configured to calculate a
   heat loss by radiation based on the first temperature and
   the ambient temperature, and obtain the final body
   temperature by adding the estimated body temperature
   and the heat loss due to the ambient temperature and
   subtracting the heat loss by radiation, and
wherein a vertical distance between the first temperature
   sensor and a surface of the body skin is less than or
   equal to 5 mm, a vertical distance between the first
   temperature sensor and the second temperature sensor
   is less than or equal to 10 mm, and a vertical distance
   between the second temperature sensor and the third
   temperature sensor is in a range of 10 mm to 50 mm.

* * * * *